US 12,048,631 B2

United States Patent
Song et al.

(10) Patent No.: US 12,048,631 B2
(45) Date of Patent: Jul. 30, 2024

(54) PAD PROSTHESIS AND ARTIFICIAL KNEE PROSTHESIS HAVING SAME

(71) Applicants: Beijing Naton Medical Technology Holdings Co., Ltd., Beijing (CN); Tianjin Zhengtian Medical Instrument Co., Ltd, Tianjin (CN)

(72) Inventors: Dayong Song, Beijing (CN); Jian Wang, Beijing (CN); Senyuan Hu, Tianjin (CN); Xiang Dong, Beijing (CN); Shufu Xu, Tianjin (CN)

(73) Assignees: BEIJING NATON MEDICAL TECHNOLOGY HOLDINGS CO., LTD., Beijing (CN); TIANJIN ZHENGTIAN MEDICAL INSTRUMENT CO., LTD, Tianjin (CN)

( * ) Notice: Subject to any disclaimer, the term of this patent is extended or adjusted under 35 U.S.C. 154(b) by 58 days.

(21) Appl. No.: 17/373,253

(22) Filed: Jul. 12, 2021

(65) Prior Publication Data

US 2022/0023052 A1    Jan. 27, 2022

(30) Foreign Application Priority Data

Jul. 24, 2020   (CN) .......................... 202010724670.3
Jul. 24, 2020   (CN) .......................... 202021494460.1

(51) Int. Cl.
*A61F 2/38*    (2006.01)
*A61F 2/30*    (2006.01)

(52) U.S. Cl.
CPC .... *A61F 2/389* (2013.01); *A61F 2002/30331* (2013.01); *A61F 2002/30428* (2013.01); *A61F 2002/305* (2013.01)

(58) Field of Classification Search
CPC . A61F 2/3868; A61F 2/389; A61F 2002/3895
See application file for complete search history.

(56) References Cited

U.S. PATENT DOCUMENTS 5,702,447 A * 12/1997 Walch ................... A61F 2/4081
                                                    606/327
5,935,175 A *  8/1999 Ostiguy, Jr. ............... A61F 2/34
                                                  623/22.28
6,004,352 A * 12/1999 Buni ....................... A61F 2/389
                                                  623/20.33

(Continued)

FOREIGN PATENT DOCUMENTS

FR     2654613 A1 *  5/1991    ............... A61F 2/38
FR     2836821 A1 *  9/2003    ............... A61F 2/38
FR     2908039 A1 *  5/2008    ............... A61F 2/38

*Primary Examiner* — Melanie R Tyson
*Assistant Examiner* — Cassidy N Stuhlsatz
(74) *Attorney, Agent, or Firm* — Hodgson Russ LLP (57) ABSTRACT

A pad prosthesis includes a body, a protrusion portion and a snap. The body has a first surface, and the first surface includes a front edge, a curved edge, a rear edge and a straight edge connected sequentially. The protrusion portion is arranged on the first surface of the body. The snap is arranged on the first surface of the body, and the snap extends along a second direction, an angle between the second direction and the first direction is an acute angle. The pad prosthesis according to the present application may be applied in an artificial knee prosthesis.

9 Claims, 7 Drawing Sheets

(56) References Cited

U.S. PATENT DOCUMENTS

| | | | |
|---|---|---|---|
| 2002/0068979 A1* | 6/2002 | Brown | A61F 2/38 |
| | | | 623/20.3 |
| 2004/0143332 A1* | 7/2004 | Krueger | A61B 17/1604 |
| | | | 606/90 |
| 2014/0067076 A1* | 3/2014 | Collazo | A61F 2/389 |
| | | | 623/20.32 |
| 2014/0324179 A1* | 10/2014 | Salehi | A61F 2/389 |
| | | | 623/20.32 |
| 2019/0298543 A1* | 10/2019 | Hashida | A61B 17/56 |
| 2020/0078182 A1* | 3/2020 | Lloyd | A61F 2/389 |
| 2020/0113702 A1* | 4/2020 | Sanford | A61F 2/389 |

* cited by examiner

PAD PROSTHESIS AND ARTIFICIAL KNEE PROSTHESIS HAVING SAME

CROSS-REFERENCE TO RELATED APPLICATION

This application claims priority to and benefits of Chinese Patent Application Serial No. 202010724670.3, filed on Jul. 24, 2020, and Chinese Patent Application Serial No. 202021494460.1, filed on Jul. 24, 2020, the entire contents of which are incorporated by reference herein.

FIELD

The present disclosure relates to a medical device, and more particularly to a pad prosthesis and an artificial knee prosthesis having the same.

BACKGROUND

Unicompartmental knee arthroplasty refers to replace a medial or lateral lesion compartment of the knee joint, and is a special form of knee replacement surgery. Compared with a total knee arthroplasty, it has the advantages of slight injury, quick recovery, joint function after the surgery being closer to a physiological state, and easier renovation.

A minimally invasive incision during unicompartmental knee surgery results in a narrow field of vision and practical operation space. For those fixed plateau products, if a tibial plateau and a pad are integrated, posterior bone cement cannot be cleaned after the product at the tibial side is mounted. In order to solve this problem, the product of the tibial plateau usually needs to be mounted first when the product at the tibial side is mounted, and then the bone cement is treated. Since there is no pad, the posterior bone cement may be treated freely, and the pad may be mounted after the treatment. Since a profile of the tibia differs greatly from that of a total knee joint, and the pad and the tibial plateau need to be firmly connected and not easy to be separated after the pad is mounted in the unicompartmental knee arthroplasty, an engaging method of the tibial plateau and the pad that meets the requirements of the unicompartmental knee arthroplasty and has a strong engaging force is needed.

SUMMARY

A pad prosthesis according to embodiments of the present disclosure includes a body, a protrusion portion and a snap. The body has a first surface. The first surface includes a front edge, a curved edge, a rear edge and a straight edge connected sequentially. The front edge is opposite to the rear edge in a front and rear direction, the curved edge is opposite to the straight edge in a first direction perpendicular to the front and rear direction, and a distance between the curved edge and the straight edge in the first direction increases first and then decreases along a direction from rear to front. The protrusion portion is arranged on the first surface of the body. The snap is arranged on the first surface of the body and extends along a second direction. An angle between the second direction and the first direction is an acute angle. The snap has a first end portion and a second end portion opposite each other in the second direction. The first end portion is close to the straight edge relative to the second end portion in the first direction, and the first end portion is close to a most front end of the front edge relative to the second end portion in the front and rear direction. A maximum distance between the second end portion and the front edge in the front and rear direction is a first distance, a maximum distance between the rear edge and the front edge in the front and rear direction is a second distance, and a ratio of the first distance to the second distance is 1:3 to 1:4.

An artificial knee prosthesis according to the present disclosure includes a tibial tray plateau and a pad prosthesis. The tibial tray plateau includes a bottom plate and a flange arranged on the bottom plate. An accommodation slot is defined between the bottom plate and the flange. The flange includes a front enclosure, a curved enclosure, a rear enclosure, and a straight enclosure connected sequentially. A front engaging slot and a first front recessed slot are defined in a rear surface of the front enclosure, and a rear engaging slot is defined in a front surface of the rear enclosure. The pad prosthesis includes a body, a protrusion portion and a snap. The body has a first surface. The first surface includes a front edge, a curved edge, a rear edge and a straight edge connected sequentially. The front edge is opposite to the rear edge in a front and rear direction, the curved edge is opposite to the straight edge in a first direction perpendicular to the front and rear direction, and a distance between the curved edge and the straight edge in the first direction increases first and then decreases along a direction from rear to front. The protrusion portion is arranged on the first surface of the body. The snap is arranged on the first surface of the body and extends along a second direction. An angle between the second direction and the first direction is an acute angle. The snap has a first end portion and a second end portion opposite each other in the second direction. The first end portion is close to the straight edge relative to the second end portion in the first direction, and the first end portion is close to a most front end of the front edge relative to the second end portion in the front and rear direction. A maximum distance between the second end portion and the front edge in the front and rear direction is a first distance, a maximum distance between the rear edge and the front edge in the front and rear direction is a second distance, and a ratio of the first distance to the second distance is 1:3 to 1:4. the protrusion portion of the pad prosthesis is able to be fitted in the accommodation slot, the snap of the pad prosthesis is able to be engaged in the front engaging slot, and the engaging projection portion is able to be engaged in the rear engaging slot. A first front recessed slot is defined in a rear surface of the front enclosure, and the first front protrusion of the pad prosthesis is able to be fitted in the first front recessed slot.

DETAILED DESCRIPTION

Embodiments of the present disclosure are further described, and examples of the embodiments are illustrated in the accompanying drawings. The embodiments described below with reference to the accompanying drawings are exemplary, are merely used to explain the present disclosure, and cannot be construed as a limitation to the present disclosure.

A pad prosthesis 1000 according to embodiments of the present disclosure is described below with reference to the accompanying drawings. As illustrated in FIGS. 1 to 8, the pad prosthesis 1000 according to embodiments of the present disclosure includes a body 1100, a protrusion portion 1200, and a snap 1300.

Figure 3:
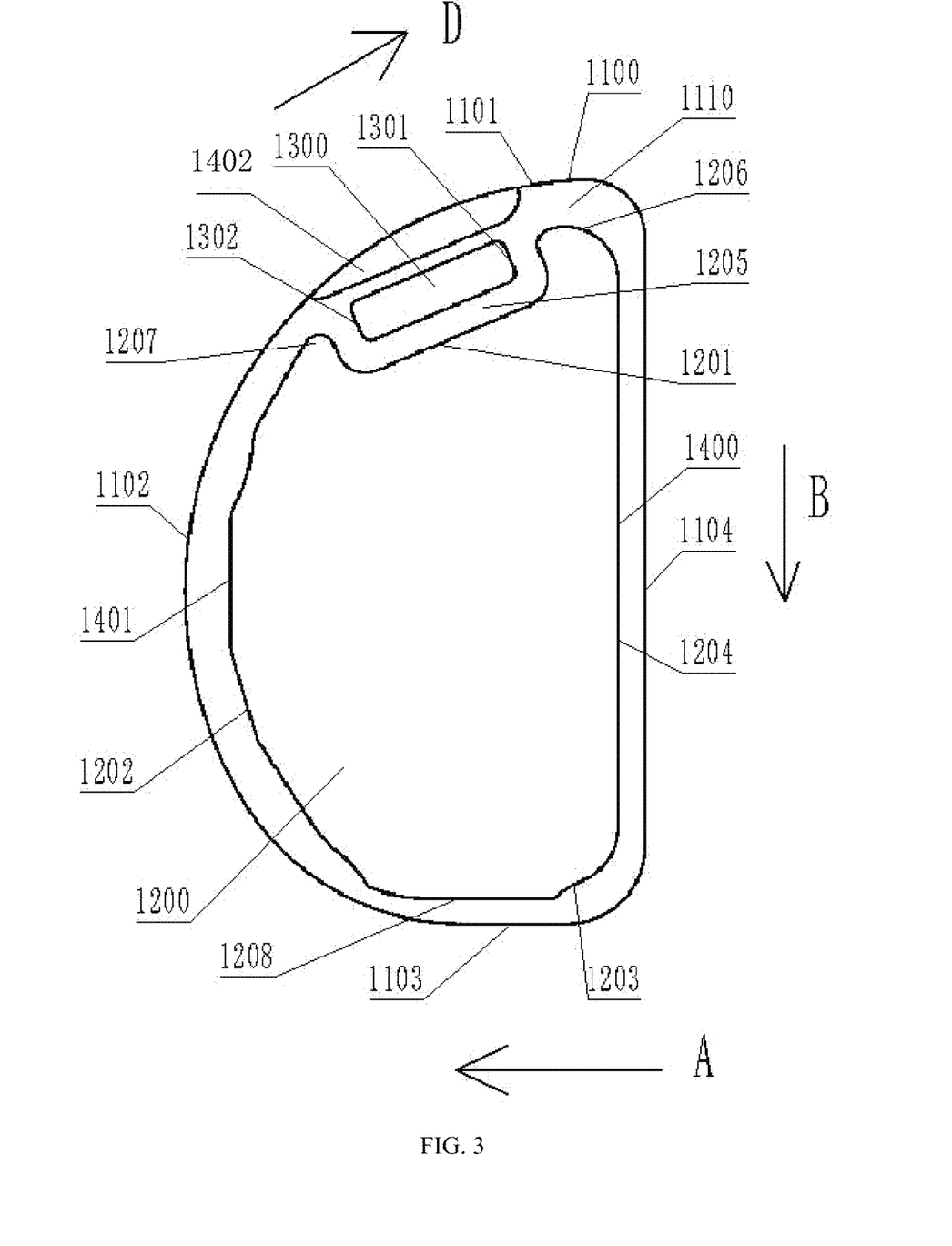
FIG. 3 is a schematic bottom view of a pad prosthesis according to an embodiment of the present disclosure.

The body 1100 has a first surface 1110 including a front edge 1101, a curved edge 1102, a rear edge 1103 and a straight edge 1104 connected sequentially. The front edge 1101 is opposite to the rear edge 1103 in a front and rear direction, the curved edge 1102 is opposite to the straight edge 1104 in a first direction, a distance between the curved edge 1102 and the straight edge 1104 in the first direction increases first and then decreases along a direction from rear to front, and the first direction is perpendicular to the front and rear direction.

The protrusion portion 1200 is arranged on the first surface 1110 of the body 1100. The snap 1300 is arranged on the first surface 1110 of the body 1100, and the snap 1300 extends along a second direction, and an angle between the second direction and the first direction is an acute angle. The snap 1300 has a first end portion 1301 and a second end portion 1302 opposite each other in the second direction, the first end portion 1301 is close to the straight edge 1104 relative to the second end portion 1302 in the first direction, and the first end portion 1301 is close to the most front end of the front edge 1101 relative to the second end portion 1302 in the front and rear direction. A maximum distance between the second end portion 1302 and the front edge 1101 in the front and rear direction is a first distance, and a maximum distance between the rear edge 1103 and the front edge 1101 in the front and rear direction is a second distance, and a ratio of the first distance to the second distance is 1:3 to 1:4.

The front and rear direction is the same as the front and rear direction of the human knee joint, and the first direction is the same as a medial and lateral direction of the human knee joint. The first direction is illustrated by arrow A in FIG. 3, the front and rear direction is illustrated by arrow B in FIG. 3, an up and down direction is illustrated by arrow C in FIG. 7, and the second direction is illustrated by arrow D in FIG. 3.

In unicompartmental knee arthroplasty, the pad prosthesis 1000 is mounted on a tibial tray plateau 2000, and the protrusion portion 1200 is fitted with an accommodation slot 2201 of the tibial tray plateau 2000. Since the ratio of the first distance to the second distance is 1:3 to 1:4, the snap 1300 is arranged on a first part of the first surface 1110 close to the front edge 1101. Since the distance between the curved edge 1102 and the straight edge 1104 in the first direction increases first and then decreases along a direction from rear to front, a size of the part of the first surface 1110 is relatively small in the first direction.

Therefore, a range of arrangement for the snap 1300 is relatively small, and if the snap 1300 extends along the first direction, a length of the snap 1300 is also relatively small. However, the pad prosthesis 1000 needs a relatively large engaging force provided by the snap 1300 to ensure that the pad prosthesis 1000 is difficult to separate from the tibial tray plateau 2000. The length of the snap 1300 is in proportion to the engaging force provided by the snap 1300.

In the pad prosthesis 1000 according to embodiments of the present disclosure, the snap 1300 extends along the second direction, and the angle between the second direction and the first direction is an acute angle, such that the snap 1300 may be obliquely arranged on the first surface 1110 of the body 1100 relative to the first direction. Thus, the size of the snap 1300 in the second direction is larger than that of the snap 1300 in the first direction. Therefore, compared with a snap extending in the first direction, the snap 1300 extending in the second direction has a greater length, thus providing a greater engaging force. Compared with the snap extending along the first direction, the snap 1300 extending along the second direction is obliquely arranged relative to the front and rear direction, and the snap 1300 extending along the second direction bears the force in the front and rear direction, which is not easy to cause deformation and displacement, such that the pad prosthesis 1000 may be more firmly engaged in the tibial tray plateau 2000.

Therefore, the pad prosthesis 1000 according to embodiments of the present disclosure has the advantages of strong engaging force, not easy to deform, and not easy to separate from the tibial tray plateau 2000.

As illustrated in FIGS. 1 to 8, the present application also provides an artificial knee prosthesis. A tibial tray prosthesis according to embodiments of the present disclosure includes the tibial tray plateau 2000 and the above-described pad prosthesis 1000.

The tibial tray plateau 2000 includes a bottom plate 2100 and a flange 2200.

An upper surface of the bottom plate 2100 is a flat surface, and the flange 2200 is arranged on the upper surface of the bottom plate 2100 and is formed integrally with the bottom plate 2100.

The flange 2200 includes a front enclosure 2210, a curved enclosure 2220, a rear enclosure 2230, and a straight enclosure 2240 connected sequentially. An upper surface 2211 of the front enclosure 2210 is on the same horizontal plane as at least a part of an upper surface of the straight enclosure 2240. An upper surface 2231 of the rear enclosure 2230 is located below the upper surface 2211 of the front enclosure 2210, an upper surface 2221 of the curved enclosure 2220 is a inclined surface, a front edge of the curved enclosure 2220 is connected with the upper surface 2211 of the front enclosure 2210, a rear edge of the curved enclosure 2220 is connected with the upper surface 2231 of the rear enclosure 2230, and the front edge of the curved enclosure 2220 is located above the rear edge of the curved enclosure 2220.

A height of the rear enclosure 2230 is lower than that of the front enclosure 2210, the upper surface 2221 of the curved enclosure 2220 is the inclined surface connecting the upper surface 2211 of the front enclosure 2210 and the upper surface 2231 of the rear enclosure 2230, and the curved enclosure 2220 is an enclosure whose height decreases smoothly from a front end to a rear end. After the tibial tray plateau 2000 is mounted, the upper surface of the rear end of the tibial tray plateau 2000 is relatively low, so as to increase the posterior space of the surgery, thereby increasing the space for cleaning the posterior bone cement of the surgery.

The front enclosure 2210, the curved enclosure 2220, the rear enclosure 2230 and the straight enclosure 2240 are sequentially connected and define the accommodation slot 2201 with the bottom plate.

The pad prosthesis 1000 and tibial tray plateau 2000 may be fitted with each other, and the protrusion portion 1200 may be fitted in the accommodation slot 2201. The pad prosthesis 1000 and tibial tray plateau 2000 may be fitted with each other and the protrusion portion 1200 may be fitted in the accommodation slot 2201, which refers to that, when the unicompartmental knee surgery is performed, the pad prosthesis 1000 is fitted with the tibial tray plateau 2000 so as to mount the pad prosthesis 1000 on the tibial tray plateau 2000, and the protrusion portion 1200 is fitted in the accommodation slot 2201; when the unicompartmental knee surgery is not performed, i.e., when the pad prosthesis 1000 and the tibial tray plateau 2000 are not in use, the pad prosthesis 1000 may or may not be fitted with the tibial tray plateau 2000, and the protrusion portion 1200 may or may not be fitted in the accommodation slot 2201.

Optionally, the shape of the accommodation slot 2201 is matched with the shape of the protrusion portion 1200, such that the protrusion portion 1200 may be more stably fitted in the accommodation slot 2201.

The snap 1300 may be engaged in a front engaging slot 2302. The snap 1300 may be engaged in a front engaging slot 2302, which refers to that, when the unicompartmental knee surgery is performed, the protrusion portion 1200 is fitted in the accommodation slot 2201, and the snap 1300 is engaged in the front engaging slot 2302; when the unicompartmental knee surgery is not performed, i.e., when the pad prosthesis 1000 and the tibial tray plateau 2000 are not in use, the snap 1300 may or may not be engaged in the front engaging slot 2302.

As illustrated in FIG. 3, in some embodiments, a peripheral surface of the protrusion portion 1200 includes a front surface 1201, a curved side surface 1202, a rear surface 1203, and a straight side surface 1204 connected sequentially. The straight side surface 1204 forms a first guide surface 1400, and a part of the curved side surface 1202 is parallel to the straight side surface 1204 to form the second guide surface 1401.

Figure 8:
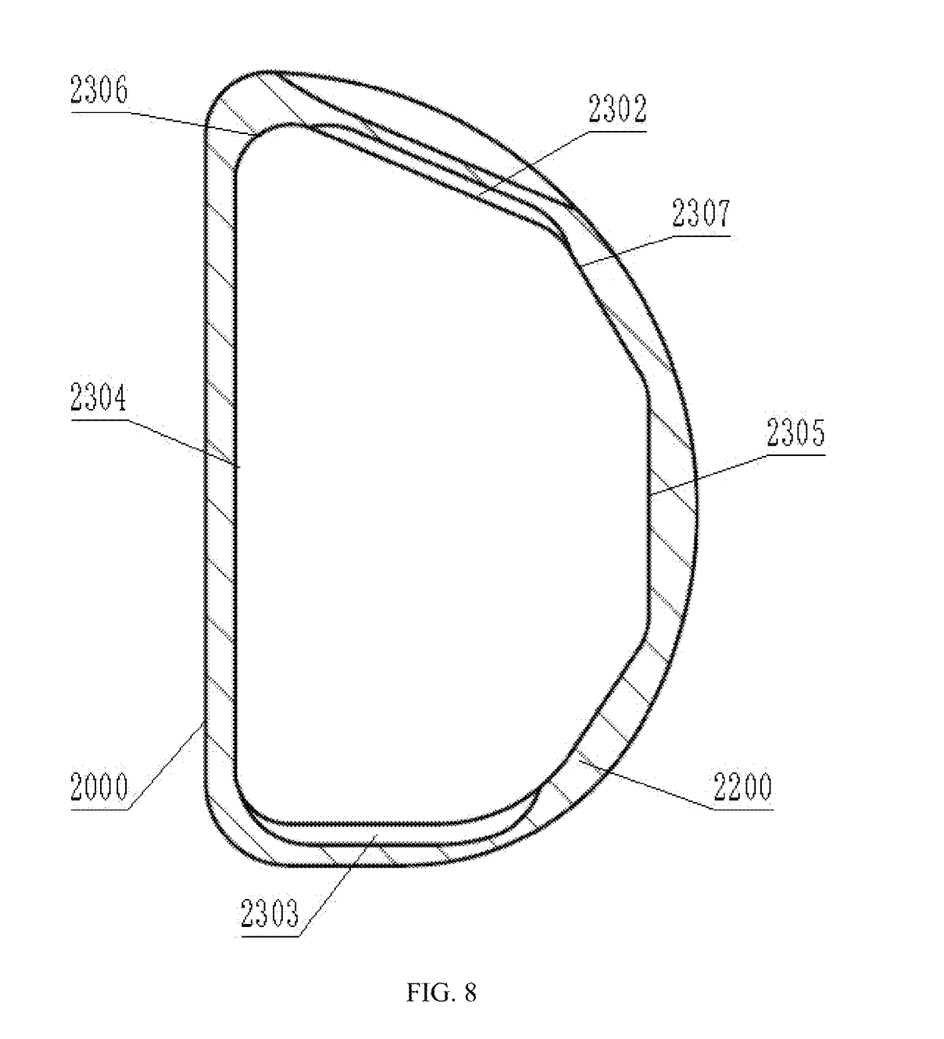
FIG. 8 is a schematic sectional view of a tibial tray plateau according to an embodiment of the present disclosure.

As illustrated in FIG. 8, an inner side surface of the straight enclosure 2240 forms a third guide surface 2304, and the inner side surface of the straight enclosure 2240 refers to a side surface of the straight enclosure 2240 adjacent to the accommodation slot 2201, i.e., the inner side surface of the straight enclosure 2240 is a part of a peripheral wall surface of the accommodation slot 2201. A third guide surface 2304 may be fitted with the first guide surface 1400 of the pad prosthesis 1000, and a part of an inner side surface of the curved enclosure 2220 is parallel to the inner side surface of the straight enclosure 2240 to form a fourth guide surface 2305. The inner side surface of the curved enclosure 2220 refers to a side surface of the curved enclosure 2220 adjacent to the accommodation slot 2201, i.e., the inner side surface of the curved enclosure 2220 is a part of the peripheral wall surface of the accommodation slot 2201. The fourth guide surface 2305 may be fitted with the second guide surface of the pad prosthesis 1000.

The third guide surface 2304 may be fitted with the first guide surface 1400, and the fourth guide surface 2305 may be fitted with the second guide surface, which refers to that, when the unicompartmental knee surgery is performed, during the pad prosthesis 1000 is mounted to the tibial tray plateau 2000, the first guide surface 1400 is in close contact with the third guide surface 2304 to move (slide) so as to be fitted with the third guide surface 2304, and the second guide surface is in close contact with the fourth guide surface 2305 to move (slide) so as to be fitted with the fourth guide surface 2305; when the unicompartmental knee surgery is not performed, i.e., when the pad prosthesis 1000 and the tibial tray plateau 2000 are not in use, the first guide surface 1400 may or may not be fitted with the third guide surface 2304, and the second guide surface may or may not be fitted with the fourth guide surface 2305.

In the process of the pad prosthesis 1000 being mounted to the tibial tray plateau 2000, the first guide surface 1400 is in close contact with the third guide surface 2304 to move (slide), and the second guide surface is in close contact with the fourth guide surface 2305 to move (slide), so as to guide the pad prosthesis 1000, and facilitate mounting of the pad prosthesis 1000 into the tibial tray plateau 2000.

Figure 2:
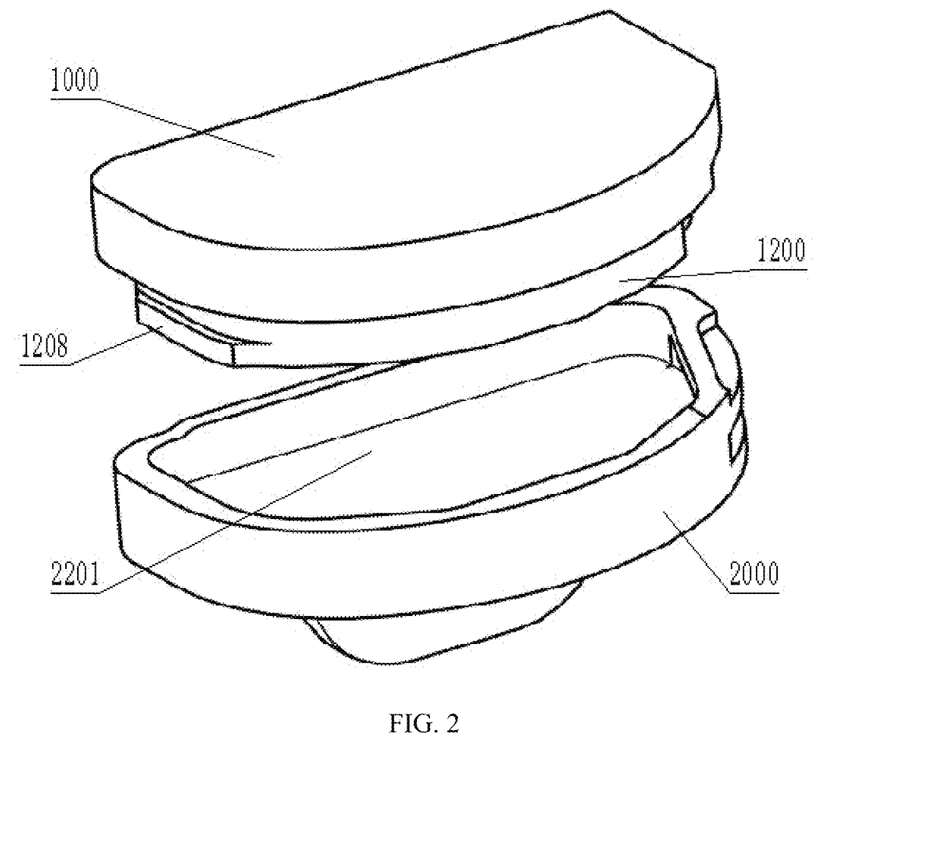
FIG. 2 is a schematic perspective view of an artificial knee prosthesis according to an embodiment of the present disclosure.

As illustrated in FIG. 2, in some embodiments, the rear surface 1203 of the protrusion portion 1200 of the pad prosthesis 1000 is provided with an engaging projection portion 1208 away from the first surface 1110. That is, the engaging projection portion 1208 is arranged on a part of the rear surface 1203 away from the first surface 1110. The front surface of the rear enclosure 2230 of the tibial tray plateau 2000 defines a rear engaging slot 2303, and the engaging projection portion 1208 may be engaged in the rear engaging slot 2303. The engaging projection portion 1208 may be engaged in the rear engaging slot 2303, which refers to that, when the unicompartmental knee surgery is performed, the protrusion portion 1200 is fitted in the accommodation slot 2201, and the engaging projection portion 1208 is engaged in the rear engaging slot 2303; when the unicompartmental knee surgery is not performed, i.e., when the pad prosthesis 1000 and the tibial tray plateau 2000 are not in use, the engaging projection portion 1208 may or may not be engaged in the rear engaging slot 2303.

The engaging projection portion 1208 is away from the first surface 1110. Thus, the rear engaging slot 2303 is arranged at a position of the rear enclosure 2230 close to the bottom plate 2100, such that a position of the rear engaging slot 2303 is matched with a position of the engaging projection portion 1208, and the position of the rear engaging slot 2303 is arranged close to the bottom plate 2100 such that the rear enclosure 2230 has higher structural strength and is more stable when accommodating the pad prosthesis 1000.

Figure 1:
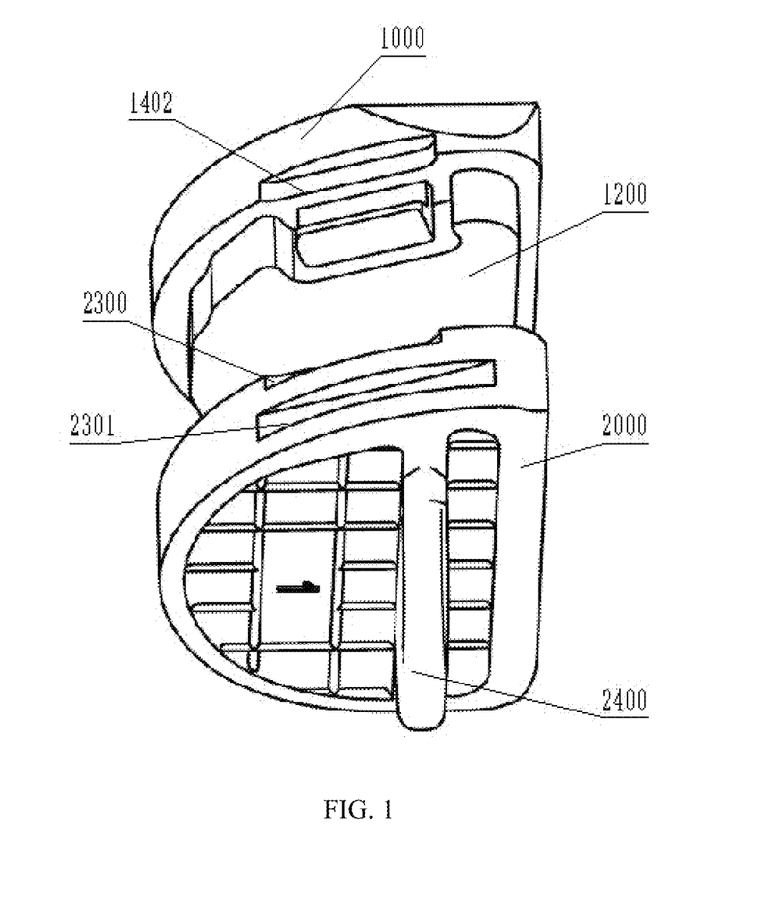
FIG. 1 is a schematic perspective view of an artificial knee prosthesis according to an embodiment of the present disclosure.

As illustrated in FIG. 1, in some embodiments, the front surface of the tibial tray plateau 2000 defines a first groove 2300 and a gripping slot 2301, the first groove 2300 is located above the gripping slot 2301, and the front surface of the body 1100 defines a second groove 1402. An upper end of the first groove 2300 is open, a lower end of the second groove 1402 is open, and the first groove 2300 and the second groove 1402 are opposite each other in an up and down direction so as to form a removing slot. Optionally, the gripping slot 2301 is arranged in a middle part of the front surface of the tibial tray plateau 2000, and the first groove 2300 is arranged in an upper part of the front surface of the tibial tray plateau 2000.

When the unicompartmental knee surgery is performed, the gripper may fix the tibial tray plateau 2000 by inserting and grasping the gripping slot 2301, and then move the tibial tray plateau 2000 to a suitable position. When it is found that the pad prosthesis 1000 and the tibial tray plateau 2000 that are engaged need to be separated, a separator is used to be inserted into the removing slot to separate the pad prosthesis 1000 and the tibial tray plateau 2000 that are engaged. After the pad prosthesis 1000 to be replaced is removed, a more suitable pad prosthesis 1000 is selected for mounting again. By the arrangement of the removing slot, it is more convenient to remove the pad prosthesis 1000 to be replaced.

As illustrated in FIG. 3, in some embodiments, the protrusion portion 1200 and the snap 1300 are spaced apart, and an avoidance slot 1205 is defined between the protrusion portion 1200 and the snap 1300 and extends along the second direction, and a maximum distance between the avoidance slot 1205 and the front edge 1101 in the front and rear direction is less than or equal to the first distance.

The avoidance slot 1205 is defined between the protrusion portion 1200 and the snap 1300, and provides an elastic deformation space for the snap 1300, such that the snap 1300 may have a greater deformability when engaged into the front engaging slot 2302, so as to facilitate smooth entrance of the snap 1300 into the front engaging slot 2302. The avoidance slot 1205 provides a necessary operational space of a cutter for the cutter to process the snap 1300, thus reducing the machining difficulty of the snap 1300.

As illustrated in FIG. 3, optionally, the peripheral surface of the protrusion portion 1200 includes the front surface 1201, the curved side surface 1202, the rear surface 1203 and the straight side surface 1204 connected sequentially. The front surface 1201 includes a first front protrusion 1206 thereon, and the first front protrusion 1206 is located between the straight side surface 1204 and a slot surface of the avoidance slot 1205, and a part of the first front protrusion 1206 is located at a front side of the snap 1300. Specifically, a distance from a most front end of the first front protrusion 1206 to a most front end of the front edge 1101 is less than a distance from a most front end of the snap 1300 to the most front end of the front edge 1101. The front surface 1201 also includes a second front protrusion 1207 located between the curved side surface 1202 and a slot surface of the avoidance slot 1205.

As illustrated in FIG. 8, a first front recessed slot 2306 is defined in a rear surface of the front enclosure 2210 and is fitted with the first front protrusion 1206. When the pad prosthesis 1000 is engaged in the tibial tray plateau 2000, the first front protrusion 1206 and the first front recessed slot 2306 are fitted, which may reduce a movement distance of the pad prosthesis 1000 in the front and rear direction under an action of force.

The rear surface of the front enclosure 2210 defines a second front recessed slot 2307 fitted with the second front protrusion 1207. When the pad prosthesis 1000 is engaged in the tibial tray plateau 2000, the second front protrusion 1207 and the second front recessed slot 2307 are fitted, which may reduce the movement distance of the pad prosthesis 1000 in the front and rear direction under the action of force.

The first front protrusion 1206 is fitted with the first front recessed slot 2306, and the second front protrusion 1207 is fitted with the second front recessed slot 2307, which refers to that, when the unicompartmental knee surgery is performed, the first front protrusion 1206 is fitted in the first front recessed slot 2306, and the second front protrusion 1207 is fitted in the second front recessed slot 2307; when the unicompartmental knee surgery is not performed, i.e., when the pad prosthesis 1000 and the tibial tray plateau 2000 are not in use, the first front protrusion 1206 may or may not be fitted with in the first front recessed slot 2306, and the second front protrusion 1207 may or may not be fitted in the second front recessed slot 2307.

The first front protrusion 1206 is fitted with the first front recessed slot 2306, and the second front protrusion 1207 is fitted with the second front recessed slot 2307, such that a relative displacement of the pad prosthesis 1000 and the tibial tray plateau 2000 is relatively small in the front and rear direction, which has little impact on human body and ensures a normal operation of the prosthesis.

As illustrated in FIG. 3, in some embodiments, the angle between the second direction and the first direction is greater than or equal to 25 degrees and less than or equal to 35 degrees. Optionally, the angle between the second direction and the first direction is 30 degrees.

Since the distance between the curved edge 1102 and the straight edge 1104 in the first direction increases first and then decreases along a direction from rear to front, the size of the first part of the first surface 1110 in the first direction is relatively small. Therefore, the range of arrangement for the snap 1300 is relatively small. If the shape of a front end of the body 1100, the need to increase the length of the snap 1300, and the need to save a suitable space for the first front protrusion 1206 in the first direction are taken into account, the best angle value for the angle between the second direction and the first direction is 30 degrees, and an appropriate angle selection range for the angle between the second direction and the first direction is greater than 25 degrees and less than 35 degrees.

The snap 1300 extends along the second direction and that is the length direction of the snap 1300 is the same as the second direction. The length of the snap 1300 is in proportion to the engaging force of the snap 1300. The length of the snap 1300 obliquely arranged is longer, and the engaging force of the snap 1300 is stronger. When the angle between the second direction and the first direction is between 25 degrees and 35 degrees, the length of the snap 1300 is relatively long, and the snap 1300 may provide a strong engaging force.

In some embodiments, a maximum distance between the first end portion 1301 and the second end portion 1302 in the second direction is 6 mm-12.5 mm, and that is, the length of the snap 1300 in the second direction is 6 mm-12.5 mm, which may meet the engaging force required by the snap 1300. Optionally, the maximum distance between the first end portion 1301 and the second end portion 1302 in the second direction is 8.5 mm, and that is, the length of the snap 1300 in the second direction is 8.5 mm, which may meet the engaging force required by the snap 1300, and save a suitable space for the first front protrusion 1206 in the first direction.

Figure 7:
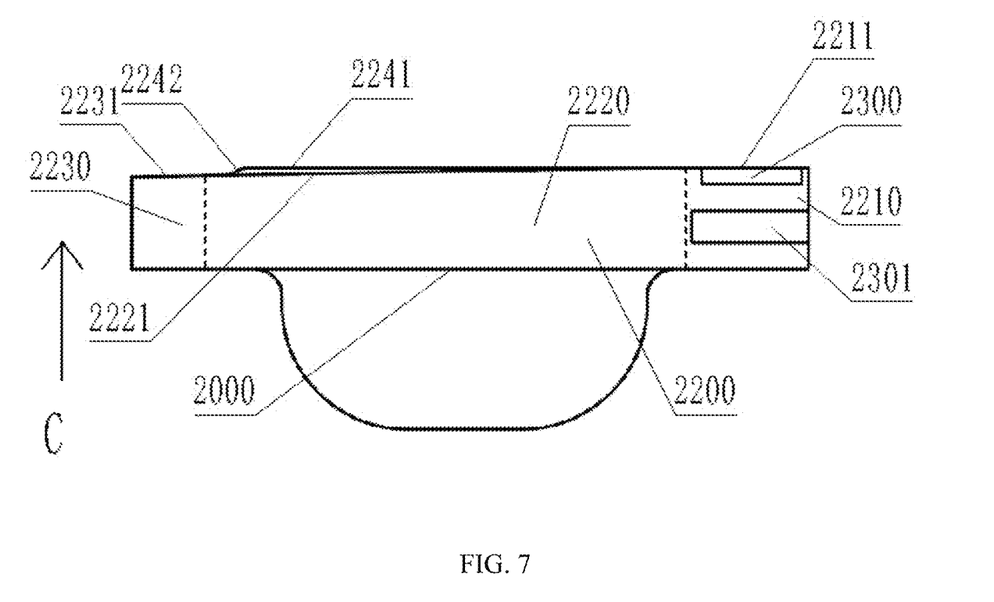
FIG. 7 is a schematic side view of a curved enclosure of a tibial tray plateau according to an embodiment of the present disclosure.

Optionally, when the length of the snap 1300 in the second direction is 8.5 mm, and the angle between the second direction and the first direction is 30 degrees, the snap 1300 has a strong engaging force while the first front protrusion 1206 has a relatively good effect on reducing the movement distance of the pad prosthesis 1000 in the front and rear directions under the action of the force. As illustrated in FIG. 7, in some embodiments, the angle between the upper surface 2221 of the curved enclosure 2220 and a horizontal plane is between 1 and 3 degrees. Since the angle between 1 and 3 degrees is small, the rear edge of the curved enclosure 2220 and the upper surface 2231 of the rear enclosure 2230 will not be too low, and sufficient structural strength is provided when the front surface of the rear enclosure 2230 is slotted. A gap generated between the upper surface 2221 of the curved enclosure 2220 and the upper surface 2231 of the rear enclosure 2230 with the first surface 1110 is small, reducing the possibility that the fit between the pad prosthesis 1000 and the tibial tray plateau 2000 becomes loose due to the gap. Moreover, the fit between the snap 1300 and the front engaging slot 2302, the fit between the protrusion portion 1200 and the accommodation slot 2201, and the fit between the engaging projection portion 1208 and the rear engaging slot 2303 enables the pad prosthesis 1000 and the tibial tray plateau 2000 to be not easy to loosen when they are engaged together, avoiding the problem that the fit between the pad prosthesis 1000 and the tibial tray plateau 2000 becomes loose due to the gap.

Figure 4:
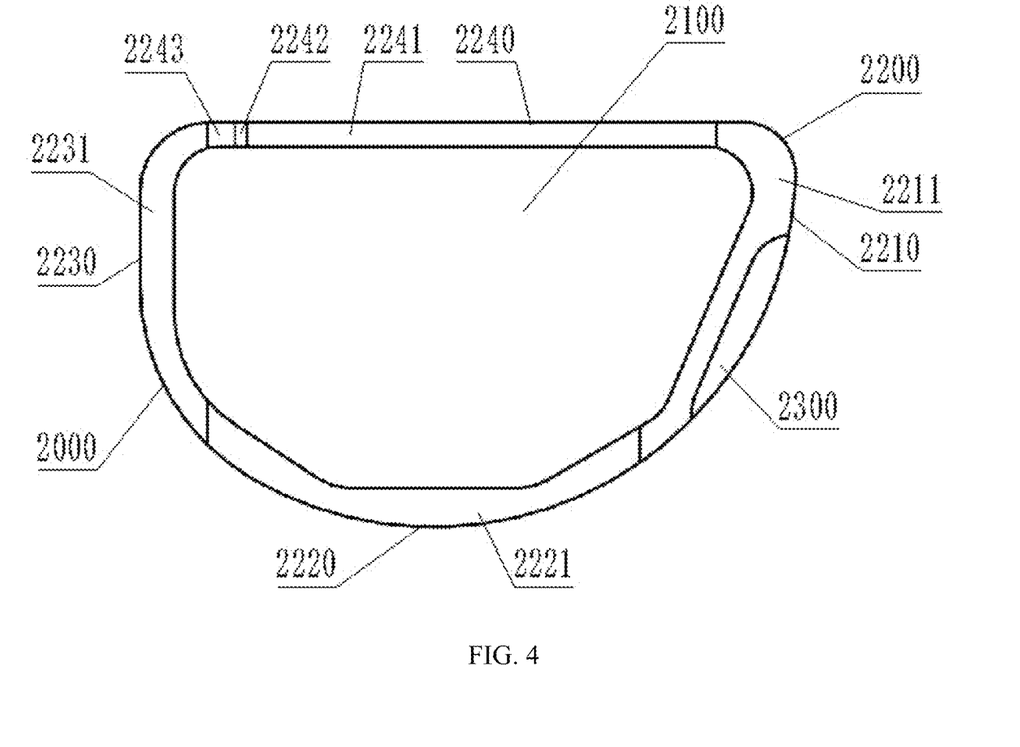
FIG. 4 is a schematic top view of a tibial tray plateau according to an embodiment of the present disclosure.

As illustrated in FIG. 4, in some embodiments, the upper surface of the straight enclosure 2240 includes a first flat surface 2241, a connecting inclined surface 2242 and a second flat surface 2243. A front edge of the first flat surface 2241 is connected with the upper surface 2211 of the front enclosure 2210, an upper edge of the connecting inclined surface 2242 is connected with a rear edge of the first flat surface 2241, a lower edge of the connecting inclined surface 2242 is connected with a front edge of the second flat surface 2243, and a rear edge of the second flat surface 2243 is connected with the upper surface 2231 of the rear enclosure 2230.

The straight enclosure 2240 is in contact with a bone incision. Since there is no bone cement adhesion, and there is no need to clean the bone cement. Therefore, the front edge of the first flat surface 2241 is connected with the upper surface 2211 of the front enclosure 2210, and a height of the first flat surface 2241 is the same as that of the front enclosure 2210. In order to clean up the bone cement of the upper surface 2231 of the rear enclosure 2230 and save enough space, the rear edge of the second flat surface 2243 is connected with the upper surface 2231 of the rear enclosure 2230, and the height of the second flat surface 2243 is the same as that of the rear enclosure 2230. The connecting inclined surface 2242 serves to connect the first flat surface 2241 and the second flat surface 2243.

The connecting inclined surface 2242 is located at a side of the upper surface of the straight enclosure 2240 close to the rear enclosure 2230. The height of the upper surface of the first flat surface 2241 is the same as that of the front enclosure 2210. Therefore, the straight enclosure 2240 has sufficient blocking height to block the movement of the pad placed therein.

Figure 5:
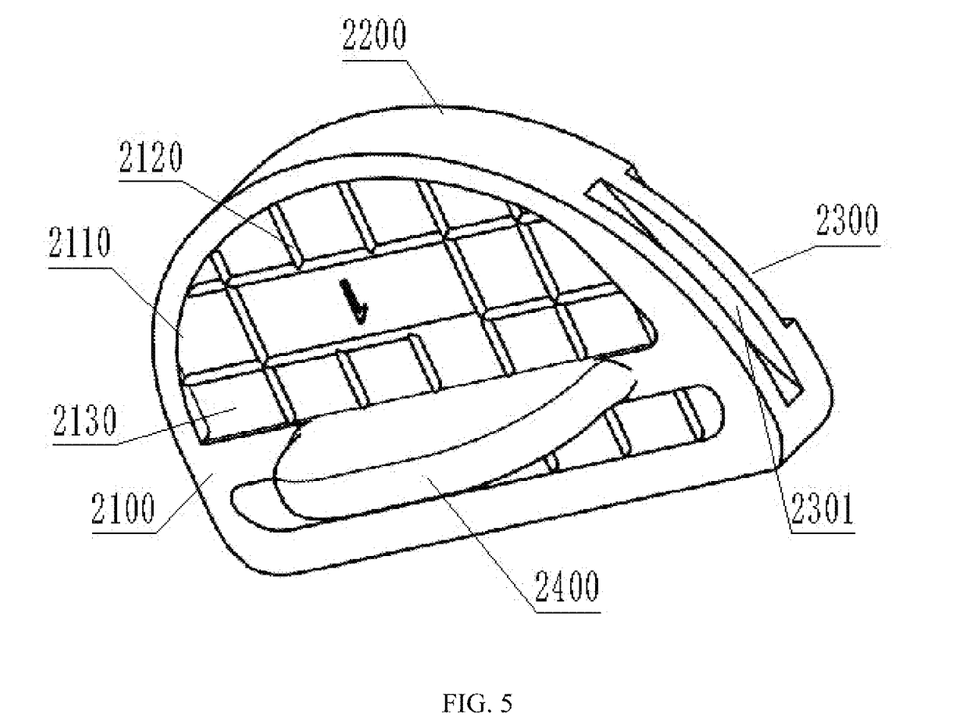
FIG. 5 is a schematic bottom view of a tibial tray prosthesis according to an embodiment of the present disclosure.
Figure 6:
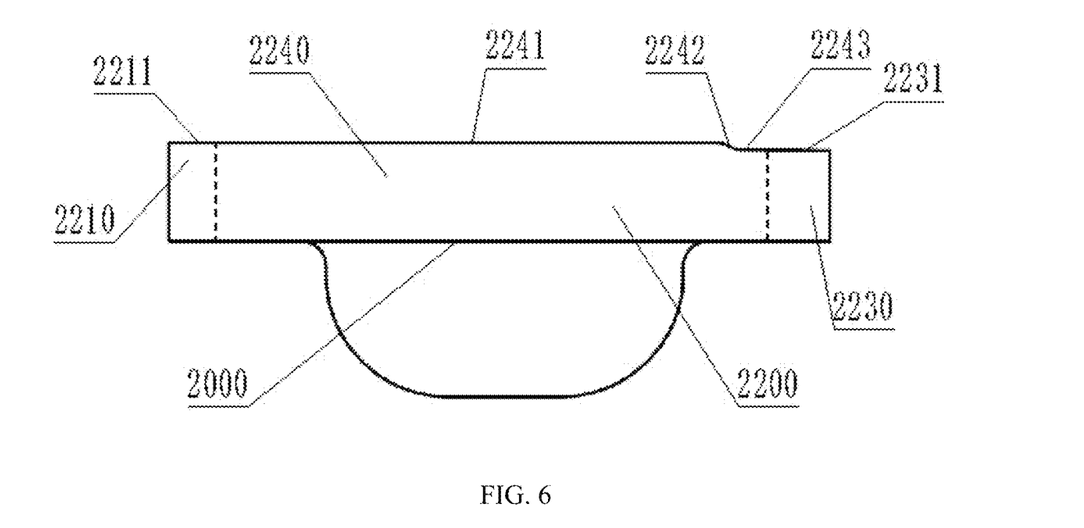
FIG. 6 is a schematic side view of a straight enclosure of a tibial tray plateau according to an embodiment of the present disclosure.

As illustrated in FIG. 5, in some embodiments, a lower surface of the bottom plate 2100 defines a bone cement slot 2110, and the tibial tray plateau 2000 further includes a plurality of dividing ribs 2120 arranged in the bone cement slot 2110 to divide the bone cement slot 2110 into a plurality of sub bone cement slots 2130.

The bone cement slot 2110 is fixed with the bone cement located below the bone cement slot 2110, and the bone cement forms a plurality of protrusions connected with it in the plurality of the sub bone cement slots 2130 of the bone cement slot 2110, such that the bone cement surface on the lower surface of the bottom plate 2100 forms a hinge lock, increasing a solidification force between the bone cement and the tibial tray plateau 2000, to have an effect of fixing the tibial tray plateau 2000.

The present disclosure also provides a tibial tray prosthesis. The tibial tray prosthesis according to embodiments of the present disclosure includes a positioning ridge 2400 and the above tibial tray plateau 2000, and the positioning ridge 2400 is connected with the tibial tray plateau 2000.

As illustrated in FIG. 5, in some embodiments, the positioning ridge 2400 is located below the tibial tray plateau 2000 and is perpendicular to the tibial tray plateau 2000. The positioning ridge 2400 and the tibial tray plateau 2000 are formed integrally. The positioning ridge 2400 plays a positioning role, such that the tibial tray plateau 2000 is in a correct position during mounting.

A pad prosthesis 1000 according to an embodiment of the present disclosure is described below with reference to FIGS. 1 to 8. The pad prosthesis 1000 includes a body 1100, a protrusion portion 1200, and a snap 1300.

The body 1100 has a first surface 1110, and the first surface 1110 is a flat surface. The first surface 1110 includes a front edge 1101, a curved edge 1102, a rear edge 1103 and a straight edge 1104 connected sequentially. The front edge 1101 is opposite to the rear edge 1103 in a front and rear direction, the curved edge 1102 is opposite to the straight edge 1104 in a first direction, a distance between the curved edge 1102 and the straight edge 1104 in the first direction increases first and then decreases along a direction from rear to front, and the first direction is perpendicular to the front and rear direction.

The protrusion portion 1200 is arranged on the first surface 1110 of the body 1100. The snap 1300 is arranged on the first surface 1110 of the body 1100, and the snap 1300 extends along a second direction, and an angle between the second direction and the first direction is an acute angle. The snap 1300 has a first end portion 1301 and a second end portion 1302 opposite each other in the second direction, the first end portion 1301 is close to the straight edge 1104 relative to the second end portion 1302 in the first direction, and the first end portion 1301 is close to the most front end of the front edge 1101 relative to the second end portion 1302 in the front and rear direction. A maximum distance between the second end portion 1302 and the front edge 1101 in the front and rear direction is a first distance, and a maximum distance between the rear edge 1103 and the front edge 1101 in the front and rear direction is a second distance, and a ratio of the first distance to the second distance is 1:3 to 1:4.

The front and rear direction is the same as the front and rear direction of the human knee joint, and the first direction is the same as a medial and lateral direction of the human knee joint. The first direction is illustrated by arrow A in FIG. 3, the front and rear direction is illustrated by arrow B in FIG. 3, an up and down direction is illustrated by arrow C in FIG. 7, and the second direction is illustrated by arrow D in FIG. 3.

In unicompartmental knee arthroplasty, the pad prosthesis 1000 is mounted on a tibial tray plateau 2000, the protrusion portion 1200 is fitted with an accommodation slot 2201 of the tibial tray plateau 2000, and the upper surface of a flange 2200 is opposite to the first surface 1110. Since the ratio of the first distance to the second distance is 1:3 to 1:4, the snap 1300 is arranged on a first part of the first surface 1110 close to the front edge 1101. Since the distance between the curved edge 1102 and the straight edge 1104 in the first direction increases first and then decreases along a direction from rear to front, a size of the part of the first surface 1110 is relatively small in the first direction.

Therefore, the pad prosthesis 1000 according to embodiments of the present disclosure has the advantages of strong engaging force, not easy to deform, and not easy to separate from the tibial tray plateau 2000.

As illustrated in FIGS. 1 to 8, the present application also provides an artificial knee prosthesis. The tibial tray prosthesis according to embodiments of the present disclosure includes the tibial tray plateau 2000 and the above pad prosthesis 1000.

The tibial tray plateau 2000 includes a bottom plate 2100 and a flange 2200.

An upper surface of the bottom plate 2100 is a flat surface, and the flange 2200 is arranged on the upper surface of the bottom plate 2100 and is formed integrally with the bottom plate 2100.

The flange 2200 includes a front enclosure 2210, a curved enclosure 2220, a rear enclosure 2230, and a straight enclosure 2240 connected sequentially. An upper surface 2211 of the front enclosure 2210 is on the same horizontal plane as at least a part of an upper surface of the straight enclosure 2240. An upper surface 2231 of the rear enclosure 2230 is located below the upper surface 2211 of the front enclosure 2210, an upper surface 2221 of the curved enclosure 2220 is an inclined surface, a front edge of the curved enclosure 2220 is connected with the upper surface 2211 of the front enclosure 2210, a rear edge of the curved enclosure 2220 is connected with the upper surface 2231 of the rear enclosure 2230, and the front edge of the curved enclosure 2220 is located above the rear edge of the curved enclosure 2220.

A height of the rear enclosure 2230 is lower than that of the front enclosure 2210, the upper surface 2221 of the curved enclosure 2220 is an inclined flat surface connecting the upper surface 2211 of the front enclosure 2210 and the upper surface 2231 of the rear enclosure 2230, and the curved enclosure 2220 is an enclosure whose height decreases smoothly from a front end to a rear end. After the tibial tray plateau 2000 is mounted, the upper surface of the rear end of the tibial tray plateau 2000 is relatively low, so as to increase the posterior space of the surgery, thereby increasing the space for cleaning the posterior bone cement of the surgery.

The front enclosure 2210, the curved enclosure 2220, the rear enclosure 2230 and the straight enclosure 2240 are sequentially connected and define the accommodation slot 2201 with the bottom plate.

The pad prosthesis 1000 and tibial tray plateau 2000 may be fitted with each other, and the protrusion portion 1200 may be fitted in the accommodation slot 2201. The shape of the accommodation slot 2201 is matched with the shape of the protrusion portion 1200, such that the protrusion portion 1200 may be more stably fitted in the accommodation slot 2201. The snap 1300 can be engaged in the front engaging slot 2302.

As illustrated in FIG. 3, a peripheral surface of the protrusion portion 1200 includes a front surface 1201, a curved side surface 1202, a rear surface 1203, and a straight side surface 1204 connected sequentially. The straight side surface 1204 forms a first guide surface 1400, and a part of the curved side surface 1202 is parallel to the straight side surface 1204 to form the second guide surface 1401.

As illustrated in FIG. 8, an inner side surface of the straight enclosure 2240 forms a third guide surface 2304, and the inner side surface of the straight enclosure 2240 refers to a side surface of the straight enclosure 2240 adjacent to the accommodation slot 2201, i.e., the inner side surface of the straight enclosure 2240 is a part of a peripheral wall surface of the accommodation slot 2201. A third guide surface 2304 may be fitted with the first guide surface 1400 of the pad prosthesis 1000, and a part of an inner side surface of the curved enclosure 2220 is parallel to the inner side surface of the straight enclosure 2240 to form a fourth guide surface 2305. The inner side surface of the curved enclosure 2220 refers to a side surface of the curved enclosure 2220 adjacent to the accommodation slot 2201, i.e., the inner side surface of the curved enclosure 2220 is a part of the peripheral wall surface of the accommodation slot 2201. The fourth guide surface 2305 may be fitted with the second guide surface of the pad prosthesis 1000.

In the process of the pad prosthesis 1000 being mounted to the tibial tray plateau 2000, the first guide surface 1400 is in close contact with the third guide surface 2304 to move (slide), and the second guide surface is in close contact with the fourth guide surface 2305 to move (slide), so as to guide the pad prosthesis 1000, and facilitate mounting of the pad prosthesis 1000 into the tibial tray plateau 2000.

As illustrated in FIG. 2, the rear surface 1203 of the protrusion portion 1200 of the pad prosthesis 1000 is provided with an engaging projection portion 1208 away from the first surface 1110. That is, the engaging projection portion 1208 is arranged on a part of the rear surface 1203 away from the first surface 1110. The front surface of the rear enclosure 2230 of the tibial tray plateau 2000 defines a rear engaging slot 2303, and the engaging projection portion 1208 may be engaged in the rear engaging slot 2303.

The engaging projection portion 1208 is away from the first surface 1110. Thus, the rear engaging slot 2303 is arranged at a position of the rear enclosure 2230 close to the bottom plate 2100, such that a position of the rear engaging slot 2303 is matched with a position of the engaging projection portion 1208, and the position of the rear engaging slot 2303 is close to the bottom plate 2100 such that the rear enclosure 2230 has higher structural strength and is more stable when accommodating the pad prosthesis 1000.

As illustrated in FIG. 1, the front surface of the tibial tray plateau 2000 defines a first groove 2300 and a gripping slot 2301, the first groove 2300 is located above the gripping slot 2301, and the front surface of the body 1100 defines a second groove 1402. An upper end of the first groove 2300 is open, a lower end of the second groove 1402 is open, and the first groove 2300 and the second groove 1402 are opposite each other in the up and down direction so as to form a removing slot. Optionally, the gripping slot 2301 is defined in a middle part of the front surface of the tibial tray plateau 2000, and the first groove 2300 is defined in an upper part of the front surface of the tibial tray plateau 2000.

When the unicompartmental knee surgery is performed, the gripper may fix the tibial tray plateau 2000 by inserting and grasping the gripping slot 2301, and then move the tibial tray plateau 2000 to a suitable position. When it is found that the pad prosthesis 1000 and the tibial tray plateau 2000 that are engaged need to be separated, a separator is used to be inserted into the removing slot to separate the pad prosthesis 1000 and the tibial tray plateau 2000 that are engaged. After the pad prosthesis 1000 to be replaced is removed, a more suitable pad prosthesis 1000 is selected for mounting again. By the arrangement of the removing slot, it is more convenient to remove the pad prosthesis 1000 to be replaced.

As illustrated in FIG. 3, the protrusion portion 1200 and the snap 1300 are spaced apart, and an avoidance slot 1205 is defined between the protrusion portion 1200 and the snap 1300 and extends along the second direction, and a maximum distance between the avoidance slot 1205 and the front edge 1101 in the front and rear direction is less than or equal to the first distance.

The avoidance slot 1205 is defined between the protrusion portion 1200 and the snap 1300, and provides an elastic deformation space for the snap 1300, such that the snap 1300 may have a greater deformability when engaged into the front engaging slot 2302, so as to facilitate smooth entrance of the snap 1300 into the front engaging slot 2302. The avoidance slot 1205 provides a necessary operational space of a cutter for the cutter to process the snap 1300, thus reducing the machining difficulty of the snap 1300.

As illustrated in FIG. 3, the peripheral surface of the protrusion portion 1200 includes the front surface 1201, the curved side surface 1202, the rear surface 1203 and the straight side surface 1204 connected sequentially. The front surface 1201 includes a first front protrusion 1206 thereon, and the first front protrusion 1206 is located between the straight side surface 1204 and a slot surface of the avoidance slot 1205, and a part of the first front protrusion 1206 is located at a front side of the snap 1300. Specifically, a distance from a most front end of the first front protrusion 1206 to a most front end of the front edge 1101 is less than a distance from a most front end of the snap 1300 to the most front end of the front edge 1101. The front surface 1201 also includes a second front protrusion 1207 located between the curved side surface 1202 and a slot surface of the avoidance slot 1205.

As illustrated in FIG. 8, a first front recessed slot 2306 is defined in a rear surface of the front enclosure 2210 and is fitted with the first front protrusion 1206. When the pad prosthesis 1000 is engaged in the tibial tray plateau 2000, the first front protrusion 1206 and the first front recessed slot 2306 are fitted, which may reduce a movement distance of the pad prosthesis 1000 in the front and rear direction under an action of force.

The rear surface of the front enclosure 2210 defines a second front recessed slot 2307 fitted with the second front protrusion 1207. When the pad prosthesis 1000 is engaged in the tibial tray plateau 2000, the second front protrusion 1207 and the second front recessed slot 2307 are fitted, which may reduce the movement distance of the pad prosthesis 1000 in the front and rear direction under the action of force.

The first front protrusion 1206 is fitted with the first front recessed slot 2306, and the second front protrusion 1207 is fitted with the second front recessed slot 2307, such that a relative displacement of the pad prosthesis 1000 and the tibial tray plateau 2000 is relatively small in the front and rear direction, which has little impact on human body and ensures a normal operation of the prosthesis.

As illustrated in FIG. 3, the angle between the second direction and the first direction is 30 degrees. The snap 1300 extends along the second direction, and that is the length direction of the snap 1300 is the same as the second direction. The length of the snap 1300 is in proportion to the engaging force of the snap 1300. The length of the snap 1300 obliquely arranged is longer, and the engaging force of the snap 1300 is stronger.

The maximum distance between the first end portion 1301 and the second end portion 1302 in the second direction is 8.5 mm, and that is, the length of the snap 1300 in the second direction is 8.5 mm, which may meet the engaging force required by the snap 1300, and save a suitable space for the first front protrusion 1206 in the first direction. The snap 1300 has a strong engaging force while the first front protrusion 1206 has a relatively good effect on reducing the movement distance of the pad prosthesis 1000 in the front and rear directions under the action of the force.

As illustrated in FIG. 7, the angle between the upper surface 2221 of the curved enclosure 2220 and a horizontal plane is 2 degrees. Since the angle of 2 degrees is small, the rear edge of the curved enclosure 2220 and the upper surface 2231 of the rear enclosure 2230 will not be too low, and sufficient structural strength is provided when the front surface of the rear enclosure 2230 is slotted. A gap generated between the upper surface 2221 of the curved enclosure 2220 and the upper surface 2231 of the rear enclosure 2230 with the first surface 1110 is small, reducing the possibility that the fit between the pad prosthesis 1000 and the tibial tray plateau 2000 becomes loose due to the gap. Moreover, the fit between the snap 1300 and the front engaging slot 2302, the fit between the protrusion portion 1200 and the accommodation slot 2201, and the fit between the engaging projection portion 1208 and the rear engaging slot 2303 enables the pad prosthesis 1000 and the tibial tray plateau 2000 to be not easy to loosen when they are engaged together, avoiding the problem that the fit between the pad prosthesis 1000 and the tibial tray plateau 2000 becomes loose due to the gap.

As illustrated in FIG. 4, the upper surface of the straight enclosure 2240 includes a first flat surface 2241, a connecting inclined surface 2242 and a second flat surface 2243, a front edge of the first flat surface 2241 is connected with the upper surface 2211 of the front enclosure 2210, an upper edge of the connecting inclined surface 2242 is connected with a rear edge of the first flat surface 2241, a lower edge of the connecting inclined surface 2242 is connected with a front edge of the second flat surface 2243, and a rear edge of the second flat surface 2243 is connected with the upper surface 2231 of the rear enclosure 2230.

The straight enclosure 2240 is in contact with a bone incision. Since there is no bone cement adhesion, and there is no need to clean the bone cement. Therefore, the front edge of the first flat surface 2241 is connected with the upper surface 2211 of the front enclosure 2210, and a height of the first flat surface 2241 is the same as that of the front enclosure 2210. In order to clean up the bone cement of the upper surface 2231 of the rear enclosure 2230 and save enough space, the rear edge of the second flat surface 2243 is connected with the upper surface 2231 of the rear enclosure 2230, and the height of the second flat surface 2243 is the same as that of the rear enclosure 2230. The connecting inclined surface 2242 serves to connect the first flat surface 2241 and the second flat surface 2243.

The connecting inclined surface 2242 is located on a side of the upper surface of the straight enclosure 2240 close to the rear enclosure 2230. The height of the upper surface of the first flat surface 2241 is the same as that of the front enclosure 2210. Therefore, the straight enclosure 2240 has sufficient blocking height to block the movement of the pad placed therein.

As illustrated in FIG. 5, a lower surface of the bottom plate 2100 is provided with a bone cement slot 2110, and the tibial tray plateau 2000 further includes a plurality of dividing ribs 2120 crossed along the front and rear direction and the first direction, and the plurality of dividing ribs 2120 are arranged in the bone cement slot 2110 to divide the bone cement slot 2110 into a plurality of sub bone cement slots 2130.

The bone cement slot 2110 is fixed with the bone cement located below the bone cement slot 2110, and the bone cement forms a plurality of protrusions connected with it in the plurality of sub bone cement slots 2130 of the bone cement slot 2110, such that the bone cement surface on the lower surface of the bottom plate 2100 forms a hinge lock, increasing a solidification force between the bone cement and the tibial tray plateau 2000, to have an effect of fixing the tibial tray plateau 2000.

The present disclosure also provides a tibial tray prosthesis. The tibial tray prosthesis according to embodiments of the present disclosure includes a positioning ridge 2400 and the above tibial tray plateau 2000, and the positioning ridge 2400 is connected with the tibial tray plateau 2000.

As illustrated in FIG. 5, in some embodiments, the positioning ridge 2400 is located below the tibial tray plateau 2000 and is perpendicular to the tibial tray plateau 2000. The positioning ridge 2400 and the tibial tray plateau 2000 are formed integrally. The positioning ridge 2400 plays a positioning role, such that the tibial tray plateau 2000 is in a correct position during mounting.

In the descriptions of embodiments of the present application, it is to be understood that, terms such as "center", "longitudinal", "lateral", "length", "width", "thickness", "upper", "lower", "front", "rear", "left", "right", "vertical", "horizontal", "top", "bottom", "inner", "outer", "clockwise", "counterclockwise", "axial," "radial", and "circumferential" should be construed to refer to the orientation as then described or as shown in the drawings under discussion, These relative terms are for convenience of description and do not require that the present disclosure be constructed or operated in a particular orientation, which cannot be construed as a limit to the present application.

In addition, terms such as "first" and "second" are used herein for purposes of description and are not intended to indicate or imply relative importance or significance or to imply the number of indicated technical features. Thus, the feature defined with "first" and "second" may comprise one or more of this feature. In the description of the present invention, "a plurality of" means two or more than two, unless specified otherwise.

In the present disclosure, unless specified otherwise, terms "mounted", "adjacent" "connected", "fixed" and the like are used broadly. For example, fixed connections, detachable connections, or integral connections; may also be mechanical or electrical connections or communication connections; may also be direct connections or indirect connections via intervening structures; may also be inner communications or interactions of two elements, which can be understood by those skilled in the art according to specific situations.

In the descriptions of the present disclosure, it should be noted that, unless otherwise expressly specified and limited, the first feature "on" or "under" the second feature may be that the first and second features are in direct contact, or that the first and second features are in indirect contact through an intermediate medium. Moreover, the first feature "up", "above" and "on" the second feature may be that the first feature is directly above or obliquely above the second feature, or merely be that the first feature has a level higher than the second feature. The first feature "down", "below" and "under" the second feature may be that the first feature is directly below or obliquely below the second feature, or merely be that the first feature has a level less than the second feature.

Reference throughout the present disclosure to terms "an embodiment," "some embodiments," "an example", "a specific example," or "some examples," means that a particular feature, structure, material, or characteristic described in connection with the embodiment or example is included in at least one embodiment or example of the present disclosure. In this specification, exemplary descriptions of aforesaid terms are not necessarily referring to the same embodiment or example. Moreover, the particular features, structures, materials, or characteristics described may be combined in any suitable manner in one or more embodiments or examples. Furthermore, in the case of non-contradiction, those skilled in the art may combine and group the different embodiments or examples described in this specification and the features of the different embodiments or examples.

Although embodiments of the present disclosure have been illustrated and described above, it should be understood that the above embodiments are illustrative and cannot be construed to limit the present disclosure, and that those skilled in the art may change, modify, alternate and vary the above embodiments within the scope of the present disclosure.

What is claimed is:

1. An artificial knee prosthesis comprising:
    a tibial tray plateau comprising a bottom plate and a flange arranged on the bottom plate, an accommodation slot being defined between the bottom plate and the flange, the flange comprising a front enclosure, a curved enclosure, a rear enclosure, and a straight enclosure connected sequentially, a front engaging slot and a first front recessed slot being defined in a rear surface of the front enclosure, and a rear engaging slot being defined in an upper surface of the rear enclosure; and
    a pad prosthesis comprising:
        a body having a first surface, the first surface comprising a front edge, a curved edge, a rear edge and a straight edge connected sequentially, the front edge being opposite to the rear edge in a front and rear direction, the curved edge being opposite to the straight edge in a first direction perpendicular to the front and rear direction, a distance between the curved edge and the straight edge in the first direction increasing first and then decreasing along a direction from rear to front;
        a protrusion portion arranged on the first surface of the body; and
        a snap arranged on the first surface of the body and extending along a second direction, an angle between the second direction and the first direction being an acute angle, the snap having a first end portion and a second end portion opposite each other in the second direction, the first end portion being close to the straight edge relative to the second end portion in the first direction, the first end portion being close to a most front end of the front edge relative to the second end portion in the front and rear direction, a maximum distance between the second end portion and the front edge in the front and rear direction being a first distance, and a maximum distance between the rear edge and the front edge in the front and rear direction being a second distance, and a ratio of the first distance to the second distance being 1:3 to 1:4,
    wherein the protrusion portion of the pad prosthesis is able to be fitted in the accommodation slot, and the snap of the pad prosthesis is able to be engaged in the front engaging slot,
    wherein a peripheral surface of the protrusion portion comprises a front surface, a curved side surface, a rear surface, and a straight side surface connected sequentially, the straight side surface forms a first guide surface, and a planar part of the curved side surface is parallel to the straight side surface to form a second guide surface,
    wherein an inner side surface of the straight enclosure forms a third guide surface, the third guide surface is able to be fitted with the first guide surface of the pad prosthesis, and a planar part of an inner side surface of the curved enclosure is parallel to the inner side surface of the straight enclosure to form a fourth guide surface, and the fourth guide surface is able to be fitted with the second guide surface of the pad prosthesis,
    wherein a front surface of the tibial tray plateau defines a first groove and a gripping slot, the first groove is located above the gripping slot, the gripping slot is formed on an outside part of the front surface of the tibial tray plateau, and a front surface of the body defines a second groove, an upper end of the first groove is open, a lower end of the second groove is open, and the first groove and the second groove are opposite each other in an up and down direction so as to form a removing slot, and wherein the artificial knee prosthesis further comprises a gripper configured to fix and move the tibial tray plateau by inserting and grasping the gripping slot.

2. The artificial knee prosthesis according to claim 1, wherein the angle between the second direction and the first direction is greater than or equal to 25 degrees and less than or equal to 35 degrees.

3. The artificial knee prosthesis according to claim 2, wherein the angle between the second direction and the first direction is 30 degrees.

4. The artificial knee prosthesis according to claim 1, wherein a maximum distance between the first end portion and the second end portion in the second direction is 6 mm-12.5 mm.

5. The artificial knee prosthesis according to claim 4, wherein the maximum distance between the first end portion and the second end portion in the second direction is 8.5 mm.

6. The artificial knee prosthesis according to claim 1, wherein a rear surface of the protrusion portion of the pad prosthesis is provided with an engaging projection portion that is spaced apart from the first surface, and the engaging projection portion is able to be engaged in the rear engaging slot.

7. The artificial knee prosthesis according to claim 1, wherein the protrusion portion and the snap are spaced apart, and an avoidance slot is defined between the protrusion portion and the snap and extends along the second direction.

8. The artificial knee prosthesis according to claim 7, wherein the front surface comprises a first front protrusion thereon, the first front protrusion is located between the straight side surface and a slot surface of the avoidance slot, a part of the first front protrusion is located at a front side of the snap, and a first front recessed slot is defined in the rear surface of the front enclosure, and the first front protrusion of the pad prosthesis is able to be fitted in the first front recessed slot.

9. The artificial knee prosthesis according to claim 1, wherein an upper surface of the curved enclosure is inclined from the front enclosure to the rear enclosure.

* * * * *